US00PP34535P2

(12) United States Plant Patent
van der Harg

(10) Patent No.: US PP34,535 P2
(45) Date of Patent: Sep. 6, 2022

(54) MINIATURE ROSE PLANT NAMED 'KORPOT109'

(50) Latin Name: *Rosa hybrida*
Varietal Denomination: KORpot109

(71) Applicant: W. KORDES' SÖHNE Rosenschulen GmbH & Co KG, Klein Offenseth-Sparrieshoop (DE)

(72) Inventor: Pieter van der Harg, Vierpolders (NL)

(73) Assignee: W. KORDES' SÖHNE Rosenschulen GmbH & Co KG, Klein Offenseth-Sparrieshoop (DE)

( * ) Notice: Subject to any disclaimer, the term of this patent is extended or adjusted under 35 U.S.C. 154(b) by 0 days.

(21) Appl. No.: 17/388,360

(22) Filed: Jul. 29, 2021

(51) Int. Cl.
*A01H 5/02* (2018.01)
*A01H 6/74* (2018.01)

(52) U.S. Cl.
USPC ..... Plt./121

(58) Field of Classification Search
USPC ..... Plt./121, 128
CPC ... A01H 5/02; A01H 5/00; A01H 6/74; A01H 6/749; A01H 1/107; A01H 1/121
See application file for complete search history.

(56) References Cited

U.S. PATENT DOCUMENTS

PP19,638 P2 1/2009 Kordes
PP23,954 P2 10/2013 Kordes

OTHER PUBLICATIONS

Floral Daily 2020 Dutch grower Wouter van der Harg, Leo van der Harg, presents Adele, retrieved on Sep. 30, 2021, retrieved from the Internet at https://www.floraldaily.com/article/9271463/new-kordana-mutant-opens-perspectives-for-2021/, 7 pp. (Year: 2020).*
Kordes Roses 2021, retrieved on Sep. 30, 2021, retrieved from the Internet at https://www.rosen.de/distributors/pot-roses/kordana/novelties/adele-kordana, 3 pp. (Year: 2021).*
CPVO 4.1.24 for 'Korpot109', retrieved on Jan. 27, 2022, retrieved from the internet at https://online.plantvarieties.eu/publicSearch?denomination=korpot109, 3 pp. (Year: 2022).*

* cited by examiner

*Primary Examiner* — June Hwu
(74) *Attorney, Agent, or Firm* — Panitch Schwarze Belisario & Nadel LLP; Stephany G. Small; Travis W. Bliss

(57) ABSTRACT

A new and distinct variety of miniature rose plant, referred to by its cultivar name, 'KORpot109', is disclosed. The new variety forms abundantly on a substantially continuous basis attractive, pink colored blossoms. Attractive vigorous vegetative is formed, which contrasts beautifully with the blossoms. The growth habit is compact. The new variety is well suited for providing attractive ornamentation in the landscape.

1 Drawing Sheet

Botanical/commercial classification:
Latin name—*Rosa hybrida.*
Varietal denomination—'KORpot109'.

SUMMARY OF THE INVENTION

The new variety of *Rosa hybrida* Miniature Rose Plant of the present invention was discovered as a branch mutation of the variety 'KORpot001' (U.S. Plant Pat. No. 23,954) in April 2020 in a greenhouse setting in Vierpolders, The Netherlands, European Union.

The parentage can be summarized as follows:

branch mutation of 'KORpot001'

It was found that the new variety of rose plant of the present invention possesses the following combination of characteristics:

(a) displays attractive, pink colored blossoms,
(b) exhibits a compact growth habit, and
(c) forms vigorous vegetation.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, the 'KORpot001' variety (i.e., the parental variety) displays cream apricot colored flowers, whereas the new variety displays pink colored flowers and the new variety exhibits a more cupped shaped flower and a more compact growth habit compared to the 'KORpot001' variety. Moreover, the new variety can be readily distinguished from other similar non-parental varieties. For example, the 'KORpedia' variety (U.S. Plant Pat. No. 19,638) displays white colored flowers, whereas the new variety displays pink colored flowers.

The new variety has been found to undergo asexual propagation in Klein Offenseth-Sparrieshoop, Germany by a number of routes, such as vegetative cuttings. Asexual propagation techniques in Germany, such as vegetative cuttings, have shown that the characteristics of the new variety are homogeneous, stable, and strictly transmissible by such asexual propagation from one generation to another. Accordingly, the new variety undergoes asexual propagation in a true-to-type manner.

The new variety has been named 'KORpot109'.

The new variety was first offered for sale on August 2020 by the inventor or another who obtained the new variety directly or indirectly from the inventor.

BRIEF DESCRIPTION OF THE PHOTOGRAPHS

The accompanying photograph shows, as nearly true as it is reasonably possible to make the same in color illustrations of this character, a typical specimen of the new variety. The illustrated rose plant of the new variety was approximately twelve weeks of age and was observed at Klein Offenseth-Sparrieshoop, Germany while growing indoors on its own roots in a 10.5 cm container.

Drawing—illustrates a specimen of a plant displaying floral buds and flowers at varying points of opening.

DETAILED BOTANICAL DESCRIPTION

The chart used in the identification of colors is that of The Royal Horticultural Society (R.H.S. Colour Chart, 2015 edition). The terminology which precedes reference to the chart has been added to indicate the corresponding color in more common terms. The description is based on the observation of a one-year-old specimen of the new variety, observed during July 2021, while growing in a one-gallon container on its own roots in a greenhouse in Cochranville, Pa.

Commercial classification: Miniature Rose Plant.

Plant:

*Habit*.—Compact.

*Height*.—Approximately 24.0 cm on average.

*Width*.—Approximately 22.0 cm on average.

Branches:

*Stem color*.—Commonly near Green Group 137C.

*Length*.—Main stems: approximately 24.0 cm on average. — secondary stems: approximately 9.0 cm on average.

*Texture*.—Glabrous.

*Thorns*.—Young thorns: moderate; color is commonly near Greyed-Yellow Group 160B; length is approximately 5.0 mm on average; and width is approximately 2.0 mm on average at point of attachment.

Foliage:

*Young foliage color*.—Upper surface: commonly near Green Group 137A with indistinguishable venation. — under surface: commonly a blend of near Yellow-Green Group 146B and near Greyed-Orange Group 176C, with venation of near Green Group 138A.

*Old foliage color*.—Upper surface: commonly near Green Group 139A with venation of near Green Group 137B. — under surface: commonly near Green Group 138B with venation of near Green Group 138C.

*Petiole*.—Upper surface: texture is smooth; color is commonly near Green Group 137A. — under surface: texture is mostly smooth with sparse prickles; color is commonly near Green Group 138B.

*Rachis*.—Color: upper surface is commonly near Green Group 137A, under surface is commonly near Green Group 138A.

*Stipules*.—Length: approximately 7.0 mm on average. — width: approximately 3.0 mm on average. — margin: entire to erose. — color: upper surface is commonly near Green Group 137B, under surface is commonly near Green Group 137C.

5-*Leaflet leaf*.—Length: approximately 8.0 cm on average. — width: approximately 5.5 cm on average.

*Leaflet arrangement*.—Odd-pinnate.

Leaflets:

*Number of leaflets*.—3, 5, and 7.

*Shape*.—Ovate; apex is acute; and base is rounded.

*Leaflet margin*.—Serrate.

*Margin undulation*.—Intensity is strong.

*Glossiness of upper side of leaflet*.—Glossy, intensity is medium.

*Venation pattern*.—Reticulate.

*Texture*.—Upper and under surfaces is smooth.

*Terminal leaflet*.—Length: approximately 4.5 cm on average. — width: approximately 2.5 cm on average.

*Lower leaflet*.—Length: approximately 2.0 cm on average. — width: approximately 1.5 cm on average.

Inflorescence:

*Number of flowers*.—Generally about 13 flowers at various stages of openness on average on a plant at once.

*Number of blooms per stem*.—Typically 1 bloom per stem on average.

*Peduncle*.—Length: approximately 3.5 cm on average. — diameter: approximately 3.0 mm on average. — surface texture: glabrous. — strength: strong. — color: commonly near Yellow-Green Group 144A.

*Sepals*.—Number: commonly 5. — length: approximately 2.0 cm on average. — width: approximately 0.5 cm on average. — margin: entire with occasional extensions on two or three sepals measuring approximately 7.0 mm in length on average and 2.0 mm in width on average. upper surface color and texture: commonly near Yellow-Green Group 144A; covered in short pubescence. — under surface color and texture: commonly near Yellow-Green Group 144A; puberulent. — shape: lanceolate. — apex: acute to aristate. — base: truncate or flat as it joins the receptacle.

*Bud*.—Shape: globular to ovoid. — length: approximately 2.5 cm on average. — width: approximately 2.0 cm on average. — color when opening: commonly near Red Group 54B.

*Flower*.—Diameter: approximately 6.5 cm on average. — height: approximately 2.0 cm on average. — duration: flower is on the plant approximately 28 days. — form: double, cuplike. — profile: flat. — shape when viewed from the top: round. — number of petals under normal conditions: approximately 70 petals on average. — petal reflex: one by one. — shape of the petal: overall: broadly obovate. apex: rounded to cuspidate. base: rounded to cuneate. — petal length: inner petals are approximately 1.0 cm on average, outer petals are approximately 2.8 cm on average. — petal width: inner petals are approximately 8.0 mm on average, outer petals are approximately 2.0 cm on average. — petal margin: entire. — petal drop: average for the type. — fragrance: very light sweet fragrance. — petal color when first and fully open: upper surface: commonly near Red-Purple Group 62A with medium sized basal spot of commonly near Greyed-Yellow Group 160D. under surface: commonly near Red-Purple Group 65A with basal spot of commonly near Greyed-White Group 157A. — petal color when fading: upper and under surfaces: commonly near White Group N155D. — petal texture: upper and lower surfaces are glabrous. — petaloids: typically 6 per flower; color of upper surface is commonly near Red-Purple Group 65B with basal spot of near Yellow Group 4D, under surface is commonly near Red-Purple Group 65B with basal spot of near Yellow Group 4D; length is approximately 5.0 mm on average; width is approximately 3.0 mm on average; texture is smooth; margin is variable, entire to erose; shape is rounded and mostly curving inward; apex is round; base is cuneate.

*Receptacle*.—Color: commonly near Yellow-Green Group 145D. — diameter: approximately 5.0 mm on average. — surface texture: smooth. — shape: urn shaped.

*Stamen*.—Number is approximately 54 on average. — anthers: number is approximately 54 on average; color is commonly near Yellow Group 2B; length is approximately 1.5 mm on average; and shape is oval. — filaments: length is approximately 1.5 mm on average and color is commonly near Yellow Group 10B.

*Pistils*.—Arrangement is separate and free; number is approximately 70 on average. — styles: length is approximately 5.0 mm on average and color is commonly near Yellow Group 5B at the base, transitioning to Red Group 45D at the apex. — stigmas: diameter is typically less than 1.0 mm; color is commonly near Yellow-Green Group 149B; shape is fan shaped.

*Pollen*.—None observed.

*Hips/seed formation*.—None observed.

Development:

*Vegetation*.—Dark green, vigorous and strong.

*Blooming*.—Abundant and continuous.

*Hardiness*.—Unknown.

*Resistance to disease*.—Good resistance to Powdery Mildew (*Sphaerotheca pannosa*) disease under normal greenhouse growing conditions in Cochranville, Pa.

*Pest resistance/susceptibility*.—None observed to date.

Plants of the 'KORpot109' variety have not been observed under all possible environmental conditions to date. Accordingly, it is possible that the phenotypic expression may vary somewhat with changes in light intensity and duration, cultural practices, and other environmental conditions.

I claim:

1. A new and distinct variety of miniature rose plant named 'KORpot109' characterized by the following combination of characteristics:

(a) displays attractive, pink colored blossoms, (b) exhibits a compact growth habit, and (c) forms vigorous vegetation;

substantially as herein shown and described.

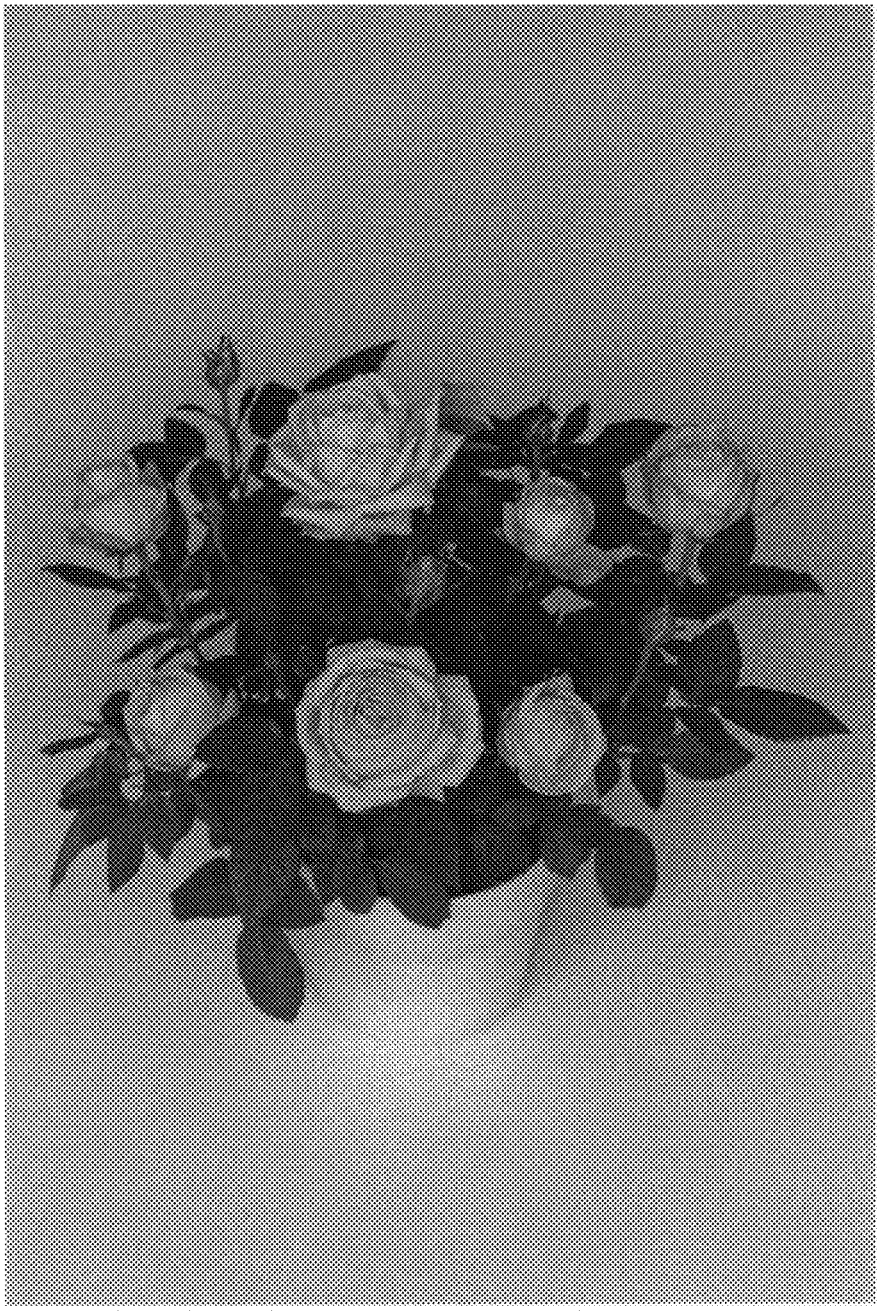

* * * * *